(12) United States Patent
Farrukh et al.

(10) Patent No.: US 9,393,313 B2
(45) Date of Patent: Jul. 19, 2016

(54) DRUG ENTRAPMENT EFFICIENCY AND SUSTAINED DRUG RELEASE OF CHLORAMPHENICOL LOADED POLYMERIC-IRON NANOPARTICLES

(71) Applicants: Muhammad Akhyar Farrukh, Lahore (PK); Adarsh Shams, Lahore (PK); Muhammad Khaleeq-ur- Rahman, Lahore (PK)

(72) Inventors: Muhammad Akhyar Farrukh, Lahore (PK); Adarsh Shams, Lahore (PK); Muhammad Khaleeq-ur- Rahman, Lahore (PK)

(*) Notice: Subject to any disclaimer, the term of this patent is extended or adjusted under 35 U.S.C. 154(b) by 0 days.

(21) Appl. No.: 14/514,055

(22) Filed: Oct. 14, 2014

(65) Prior Publication Data

US 2016/0101182 A1    Apr. 14, 2016

(51) Int. Cl.
*A61K 31/16* (2006.01)
*A61K 47/38* (2006.01)
*A61K 31/165* (2006.01)
*A61K 47/02* (2006.01)

(52) U.S. Cl.
CPC ............... *A61K 47/38* (2013.01); *A61K 31/165* (2013.01); *A61K 47/02* (2013.01)

(58) Field of Classification Search
None
See application file for complete search history.

(56) References Cited

U.S. PATENT DOCUMENTS

2007/0290175 A1* 12/2007 Kim ..................... B22F 1/0018
                                                            252/500
2010/0009007 A1*  1/2010 Darvari ................ A61K 9/5073
                                                            424/499

OTHER PUBLICATIONS

Ashraf et al (Cellulose 21:395-405, 2014).*
Behera et al (World J Nano Science and Engineering 2:196-200, 2012).*

* cited by examiner

*Primary Examiner* — Craig Ricci
(74) *Attorney, Agent, or Firm* — Sarfaraz K. Niazi

(57) ABSTRACT

This invention harvests nanocomposite which enable targeted delivery of antibiotics. Biodegradable and biocompatible polymer such as diethylaminoethyl-cellulose (DEAE-Cellulose) are used in combination with iron, which contributes its magnetic characteristics to the nanocomposite. The nanoparticles produced could be used as carriers for releasing chloramphenicol at the targeted site for sustained release.

7 Claims, 8 Drawing Sheets

DRUG ENTRAPMENT EFFICIENCY AND SUSTAINED DRUG RELEASE OF CHLORAMPHENICOL LOADED POLYMERIC-IRON NANOPARTICLES

BACKGROUND OF THE INVENTION

Conventional drug therapy showed that it is ineffective countless times, owing to high drug toxicity in systemic circulation, irregular drug distribution within human body, low permeability of tissues and elevated hydrophobicity of numerous substances that are biologically active. To overwhelm all these complications, several techniques of drugs targeting were contracted: polymeric micelles, drug-polymer conjugates, liposomes, microparticles, nanoparticles, nanocomposite.

According to some studies extremely hydrophobic drugs can be targeted to the specific site in nanoparticles formulations. Clinical trials have established these pharmacological studies, and some of these formulations are available in the market currently.

In edict to be well-designed in the therapy, nanoparticles must encounter numerous requirements: customize bio-distribution rendering targeted delivery, stability over a specified period of time, prolong circulating time, enabling active or passive targeting in the preferred region, receptiveness towards stimuli (temperature, pH, and so on). Recent research encompassing nanoparticles having magnetic characteristics have been conducted, predominantly for biotechnological applications such as sorting and separation of cells, drug delivery and resonance imaging of the magnetic nature.

During the course of drug delivery, magnetic nanoparticles loaded with drug upon presentation of an external magnetic field channel the drug to the specified site from systemic circulation leading to higher concentrations of drug at the targeted location. Ultimately enhancing the effects of drugs tremendously.

BRIEF SUMMARY OF THE INVENTION

Novel magnetic nanoparticles of magnetic basis are devised earnestly due to their vast wide uses. Increased surface area, size and morphology enable the hybrid nature of nanomaterial to demonstrate exceptional catalytic, electronic and optical characteristics. Iron oxide nanoparticles of magnetic nature are suitable candidates for sustained and/or prolonged drug delivery. Chloramphenicol is used in indications such as eye and ear infections and typhoid fever, but this drug has poor bioavailability when given orally, which is instigated by the poor solubility of the drug in the gastrointestinal tract and its early degradation. Dose-related side effects of the drug are bone marrow depression leading to hemolytic anemia and the gray baby syndrome.

DEAE-Cellulose-Fe nanocomposite and chloramphenicol-loaded nanocomposite were synthesized by sonochemical technique. Drug-loading was evaluated by UV/visible spectroscopy. Antibacterial activity was performed to analyze drug-loading on the nanocomposite.

DETAILED DESCRIPTION OF THE INVENTION

Figure 1A:
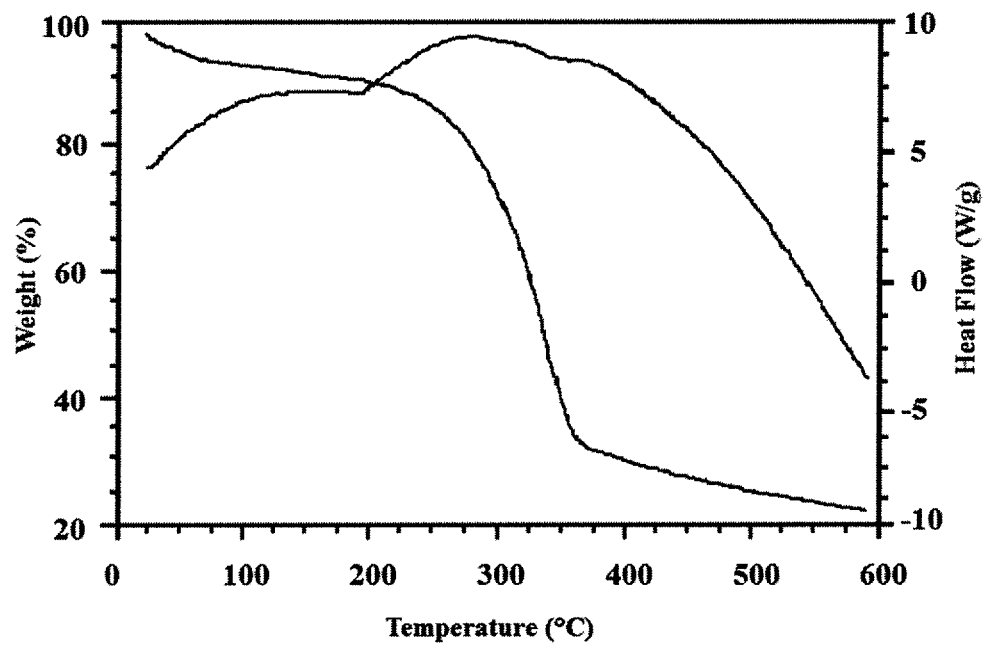
FIG. 1A depicts TGA of nanocomposite

The nanocomposite was prepared by employing sonochemical method. Diethylaminoethylcellulose (0.01 M) was added in aqueous solution of NaOH and sonicated for 30 minutes. Clear solution of (0.01 M) $FeSO_4$ in 0.1 M $H_2SO_4$ was added to the above solution at a rate of 0.5 mL/5 minutes, which lead to the formation of nanocomposite precipitates. These precipitates were centrifuged at 13,500 rpm for separation and dried at 70° C.

Nano composite (10 mg) was dispersed in 10 mL water and sonicated for 1 hour. 2 mL (10 mg) of chloramphenicol eye drops were taken with 8 mL of water and added to the above solution at a rate of 0.5 mL/1 minute. Drug-loaded nanocomposite particles, thus formed were centrifuged at 13,500 rpm and dried at 40° C. Different variants of drug-loaded nanocomposite in 1:1 ratio were formed to observe the variation in drug loading by altering the solvent system (% of ethyl acetate in water). The percentages of ethyl acetate in water were 20, 40, 60, 80 and 100%.

Fourier Transform Infra-Red spectroscopy (FTIR) This form of spectroscopy employs the principle that every atom has its own characteristic vibrations in a functional group present a molecule due to the absorption of IR radiations. The range of these frequency vibrations lies in between 400-4000 $cm^{-1}$. Literature can serve as a source for the peak values of different functional groups. Potassium bromide and a sample are taken in a ratio of 5:1 for the preparation of pallet in a pallet manufacturer. FT-IR MIDAC M2000 is the instrument used for the analysis.

X-rays are employed as a source in this technique which passes through the sample. The spectra was obtained by the diffraction of X-rays beam at an angel of 2θ. The sample would be rotated at all the conceivable planes. The intense peaks were used to calculate the mean texture size of nanocomposite via Scherrer equation. X"pert PRO, PANalytical Company was the instrument used for this particular characterization.

Concentrated beam of high energy electrons is employed in SEM that gives a combination of indications or signals at the solid sample surface. Evidence regarding chemical composition, orientation and crystalline structure and external morphology is provided by the electronic signals generated upon their interaction with the sample. S-3400N-Hitachi is the instrument used for the analysis.

Transmission Electron Microscopy (TEM) is a procedure where the electron beam is passed through an ultra thin layer of the sample, which intermingles with the sample on its way out. Electrons that pass through the sample shape an image. Using electron instead of light enables TEM imaging at higher resolution than a light microscope. Tens of thousands times smaller particles can be analyzed by electron microscope, which is smaller than the ones a light microscope can analyze. TEM microscope (Phillip CM12 microscope) was used to check the structure and particle size distribution of polymer-Fe nanoparticles.

Thermal Gravimetric Analysis (TGA) is an analysis performed in controlled atmosphere that defines changes in the sample with respect to the temperature changes. Three parameters are kept into accounts i.e. weight, temperature, and temperature change. Nanoparticles were tested at 600° C. peak temperature via instrument DSC-TGA SDT Q600 V8.3 and SDT Q600 V8.2 Build 100 was used to obtain spectra.

Nutrient broth was prepared by dissolving 0.2 g in 25 mL distilled water in erlenmeyer flask. The flask was then sterilized in an autoclave at the 121° C. for 15 minutes after applying cotton plug to cover its mouth. This growth media was utilized to prepare inoculums of all strains of bacteria. After adding a loop full of bacterial strain in it, the flask was placed in shaking incubator at 37° C. for the night. The plates were inoculated after the incubated broth was diluted up to $10^{-2}$.

0.8 g nutrient broth and 2 g of agar were added to 100 mL autoclaved water in an erlenmeyer flask. Apply cotton plug to the flask and then sterilize it in an autoclave at the 121° C. for 15 minutes. Each petri plate was poured with 15-20 mL of agar which was then solidified and inoculated with the bacterial strain. 50 μL of sample suspension was poured in wells that have the diameter of 0.4 cm. All sample suspensions were made by adding 5 mg of product in 1 mL distilled water. Zones of inhibition were observed after keeping these plates at 37° C. for 48 hours.

30 mg of CHL-loaded nanoparticles were dispersed and homogenized in 100 mL of PBS, pH 7.4 (purchased from Sigma Aldrich) which releases all entrapped CHL from the nanocomposite. Before homogenization, nanocomposite formulation was cleared from free drug molecules by washing with distilled water. Ultraviolet (UV) spectroscopy at a wavelength of 278 nm was employed for completely developing entire content of entrapped chloramphenicol in triplicates. A solution of drug-free nanocomposite (30 mg) in distilled water was employed as a reference, thus reducing the chances of interference by excipients and polymer used to prepare the nanocomposite. Following equation was utilized to evaluate drug entrapment efficiency (DEE) value, as was reported in a paper by Harilall S, Choonara Y E. et al.

$$\%DEE = D_1/D_2 * 100$$

Where $D_1$ is the actual quantity of drug (mg/100 mL) and $D_2$ is the theoretical quantity of drug (mg/100 mL) entrapped within the formulation. Precision of the results was made certain by calculating the average DEE of five samples.

An in-vitro drug release study was conducted on the basis of a paper reported by Harilall S, Choonara Y E. et al. for the zidovudine release study. CHL-loaded nanocomposite, nanocomposite and commercially available CHL were submerged in 100 mL PBS discretely and then sited these set of preparations in an orbital shaking incubator (20 rpms, 37° C.). Portions of these preparations were taken at altered time interims for 48 hours and substituted by equal quantities of buffer solution and were evaluated by UV spectroscopy for CHL absorption at a wavelength of 278 nm.

TGA Studies

FIG. 1A reveals weight loss rate increases with an increase in temperature. It is shown that the initial weight loss is 11% from 50° C. to 100° C. was due to the moisture content present in the sample. The next weight loss is observed at 200° C. to 350° C. which corresponds to the decomposition of diethylaminoethylcellulose.

FTIR Studies

Figure 2:
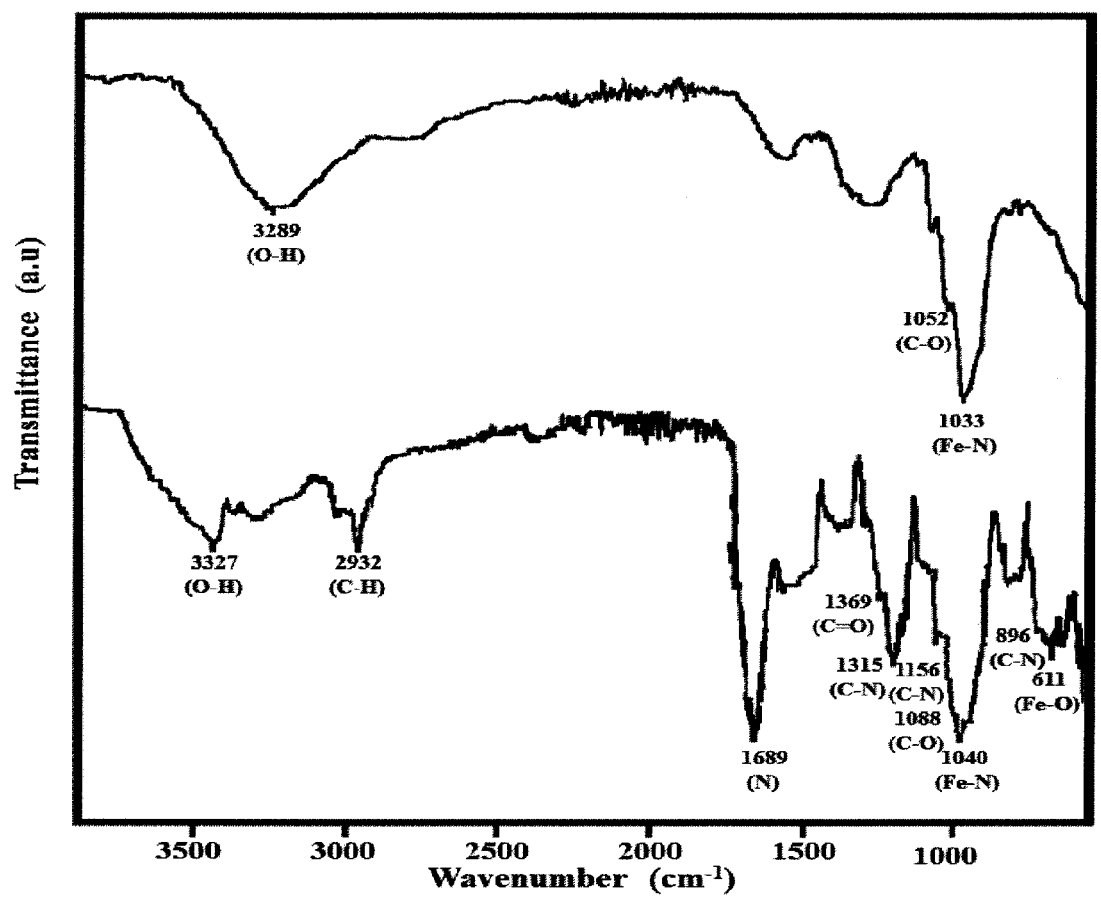
FIG. 2 depicts FTIR spectra of nanocomposite and CHL-loaded nanocomposite.

FTIR comparison of nanocomposite, CHL-loaded nanocomposite are given in FIG. 2. FTIR band ranging 3400-3100 $cm^{-1}$ represents —OH stretching vibrations. The —OH group is present in both i.e. polymer and drug. The nanocomposite peaks in FIG. 2 at 3289, 1052, 1033 $cm^{-1}$ corresponds to the peaks of —OH, C—O, Fe—N stretching vibrations present in the nanocomposite respectively. The peaks shown in FIG. 2 at 3327 $cm^{-1}$, and 611 $cm^{-1}$ correspond to the peaks of —OH, and Fe—O stretching vibrations present in the CHL-loaded nanocomposite respectively. Whereas the peaks in FIG. 2b at 2932 $cm^{-1}$ represents aromatic C—H stretching, 1689 $cm^{-1}$ represents amide I, 1369 $cm^{-1}$ represents C=O stretching mode, 1088 $cm^{-1}$ represents C—O stretching (Primary alcohol), 1040 $cm^{-1}$ represents Fe—N stretching and 896 $cm^{-1}$ corresponds to C—N stretching vibrations. Additional two peaks at 1315 and 1158 $cm^{-1}$ were observed in the CHL-loaded nanocomposite corresponding C—N stretch aromatic amines and C—N stretch aliphatic amines respectively.

TEM Studies

Figure 3A:
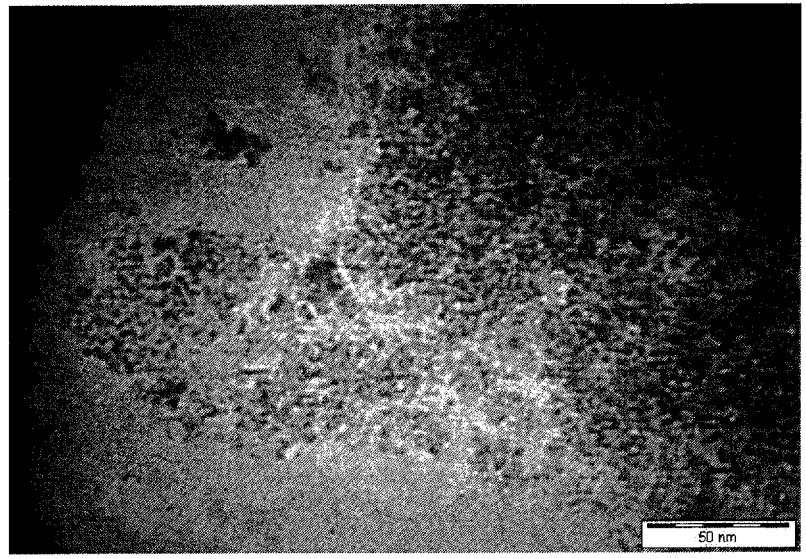
FIG. 3A depicts TEM images of CHL-loaded nanocomposite
Figure 3B:
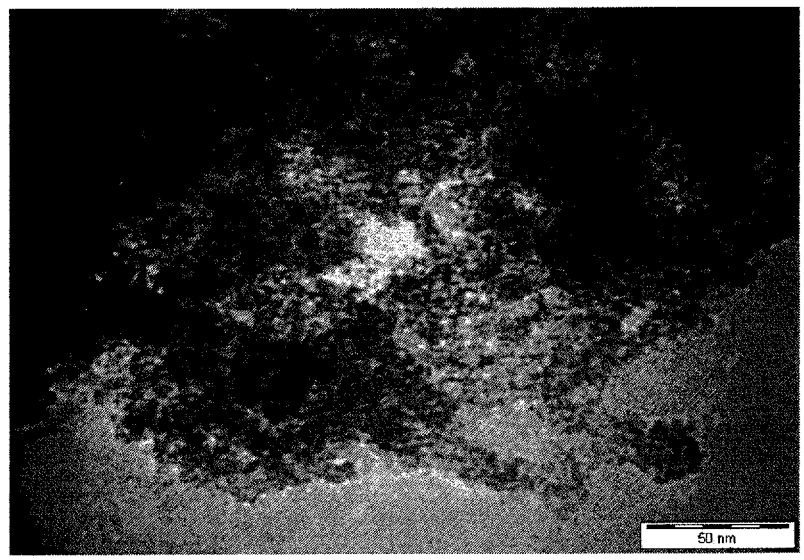
FIG. 3B depicts a nanocomposite.

The calculated particle size of nanocomposite and CHL-loaded nanocomposite was 3.66 nm as shown in FIG. 3b and 3.9 nm shown in FIG. 3a respectively.

SEM Studies

Figure 4:
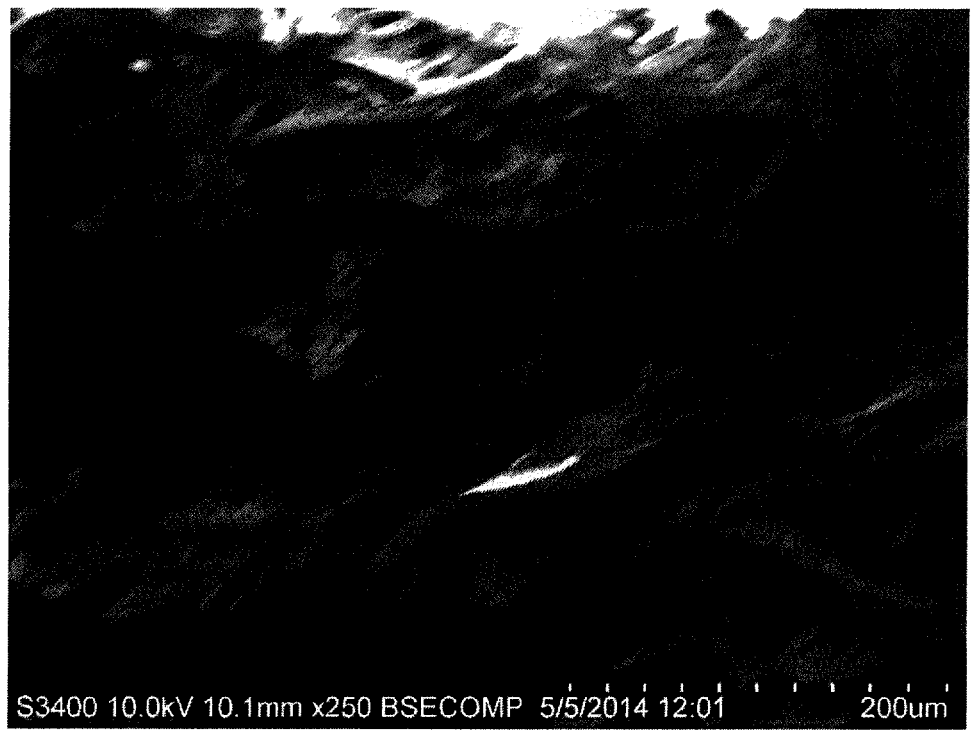
FIG. 4 depicts SEM image of DEAE-Cellulose/Fe nanocomposite.

FIG. 4 shows nanocomposite of DEAE-Cellulose/Fe. The microfibrils have a length of 120-160 μm and diameter of 15-20 μm and showed the deposition of Fe upon them forming the agglomerations.

XRD Analysis

Peaks at 2θ values of 35.7383, 58.77 and 64.8234 have hkl values of 311, 511 and 440 respectively showing the presence of Fe.

Figure 6A:
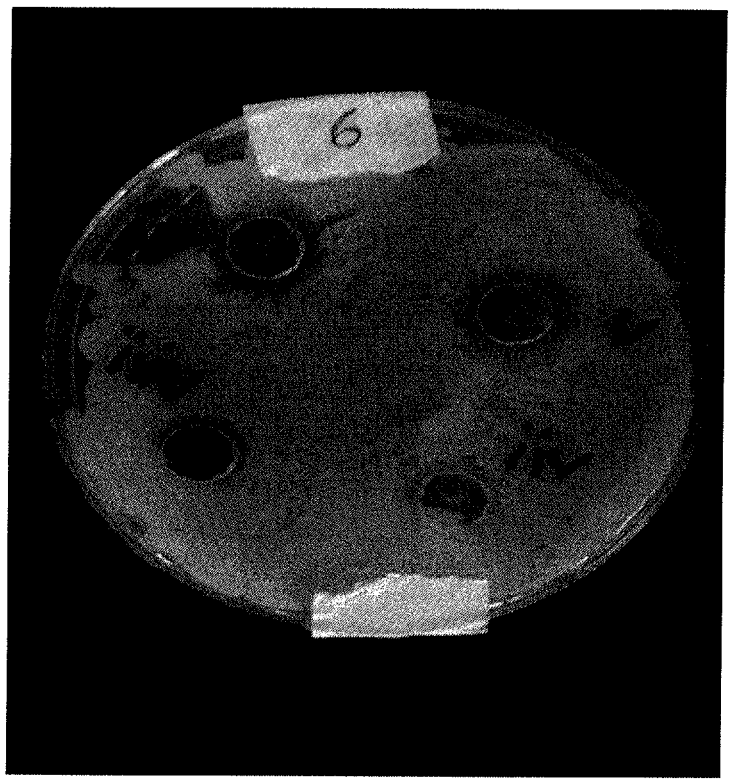
FIG. 6A depicts anti-bacterial activity of CHL-loaded nanocomposite after 24 hours.
Figure 6B:
FIG. 6B depicts anti-bacterial activity of CHL-loaded nanocomposite after 48 hours.

Anti-Bacterial Activity of CHL-Loaded Nanocomposite:

Three bacterial strains were used for anti-bacterial activity i.e. Gram-positive cocci (Separate), Gram-positive Streptococci and Gram-positive sarccina. Anti-bacterial activity of CHL-loaded nanocomposite was enhanced than commercially available CHL (0.5%). The CHL-loaded nanocomposite showed lesser anti-bacterial activity after 24 hours of incubation whereas its activity is enhanced a lot after another 24 hours of incubation as shown in FIGS. 6a and 6b respectively. Detail of antibacterial activities of CHL-loaded nanocomposite prepared under variation of solvent concentration is given in Table 1.

TABLE 1

Anti-bacterial activity of nanocomposite, CHL-loaded nanocomposite and its variants

| Bacterial strains | Nano-composite 50 μL (5 mg/mL) | CHL (Drug) | Nano-composite + Drug (N + D) | (N + D) 20% Solvent system (% EA in H₂O) | (N + D) 40% | (N + D) 60% | (N + D) 80% | (N + D) 100% |
|---|---|---|---|---|---|---|---|---|
| Gram positive cocci (Separate) | No zone of inhibition | 4 mm | 10 mm | 6 mm | 15 mm | 18 mm | 6 mm | 4 mm |
| Gram positive *Streptococci* | No zone of inhibition | 6 mm | 8 mm | 4 mm | 12 mm | 16 mm | 4 mm | 2 mm |

TABLE 1-continued

Anti-bacterial activity of nanocomposite, CHL-loaded nanocomposite and its variants

| Bacterial strains | Nano-composite 50 μL (5 mg/mL) | CHL (Drug) | Nano-composite + Drug (N + D) | Solvent system (% EA in H$_2$O) | | | | |
|---|---|---|---|---|---|---|---|---|
| | | | | (N + D) 20% | (N + D) 40% | (N + D) 60% | (N + D) 80% | (N + D) 100% |
| Gram positive *sarccina* | No zone of inhibition | 2 mm | 4 mm | 6 mm | 8 mm | 9 mm | 2 mm | 2 mm |

Figure 7:
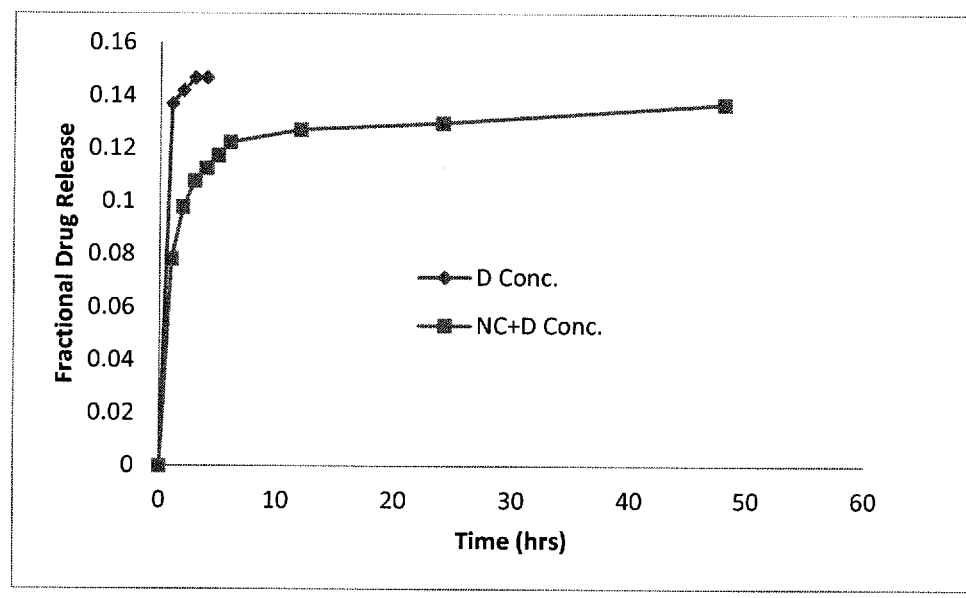
FIG. 7 depicts in-vitro drug release of commercially available CHL (represented by D Conc.) and CHL-loaded nanocomposite (represented by NC+D Conc.).

Entrapment Efficiency of Chloramphenicol-Loaded Nanoparticles and In-Vitro Drug Release Studies FIG. 7 shows that commercially available CHL demonstrated DEE of 91% in the first hour of its exposure to the PBS which was further increased to 94, 97 and 97% in the next three hours respectively. Whereas CHL-loaded nanocomposite showed a maximum of DEE of 91% in 48 hours.

Figure 1B:
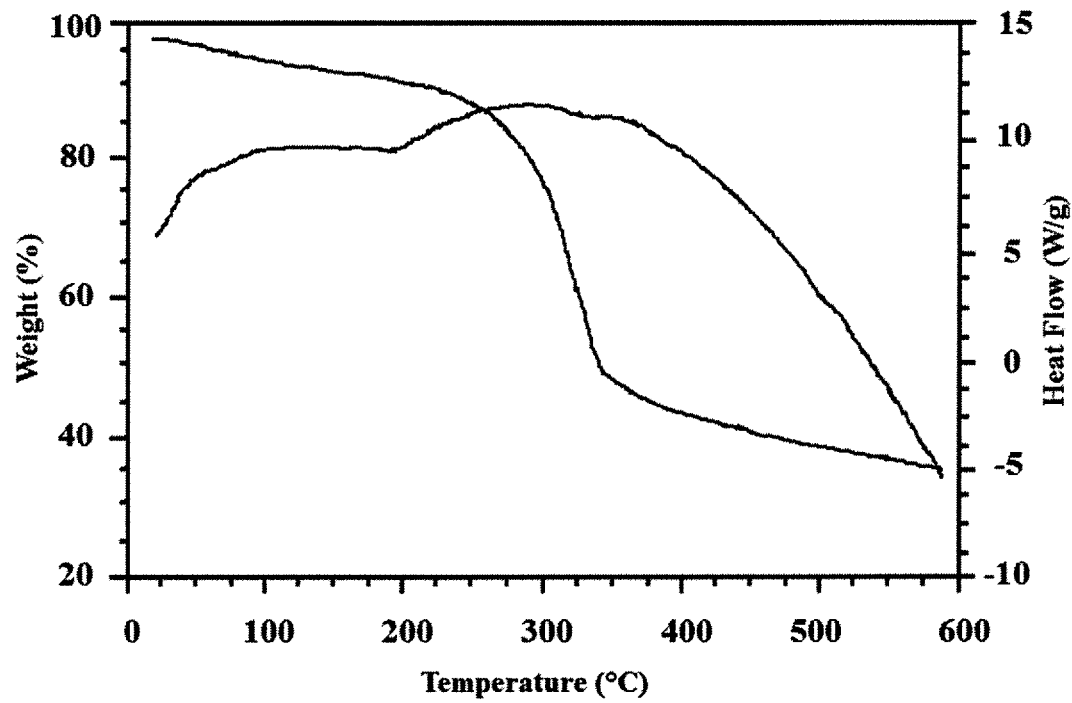
FIG. 1B depicts CHL-loaded nanocomposite

FIGS. 1A and 1B show TGA of nanocomposite and CHL-loaded nanocomposite. Qiu L. et al. (2013) reported in his paper that cellulose derivatives decompose at 200-350° C. temperature. The exothermic peak at 200-350° C. temperature observed in DSC diagram also support the evidence of polymer decomposition. Similar observations were made regarding FIG. 1B. Comparison between the figures suggest that drug-loaded nanocomposite is more thermally and chemically stable than nanocomposite itself due to the compatibility (interaction between components) of nanocomposite and drug.

FIG. 2 represents FTIR of nanocomposite and CHL-loaded nanocomposite. Gupta J. et al. 2011 reported FTIR of chloramphenicol as 3340 cm$^{-1}$ represents —OH stretching, 2927 cm$^{-1}$ represents aromatic C—H stretching, 1687 cm$^{-1}$ represents amide I, 1346 cm$^{-1}$ represents C=O stretching mode, 1071 cm$^{-1}$ represents C—O stretching (Primary alcohol) and 876 cm$^{-1}$ C—N stretching vibrations. FTIR of CHL-loaded nanocomposite showed all of the peaks discussed above. Presence of Fe—N stretching vibrations at 1033 in nanocomposite and at 1040 cm$^{-1}$ in CHL-loaded nanocomposite confirmed the formation of Fe—N bond. Weak Wander Vaal's forces of attraction are the reason for Fe—O stretching vibrations observed in CHL-loaded nanocomposite. Additional two peaks at 1315 and 1158 cm$^{-1}$ were observed in the CHL-loaded nanocomposite corresponding C—N stretch aromatic amines and C—N stretch aliphatic amines respectively that are present in CHL. FTIR of variants (i.e. nanoparticles prepared by 20, 40, 60, 80 and 100% solvent system) were similar to the FTIR of chloramphenicol-loaded nanoparticles.

Figure 5:
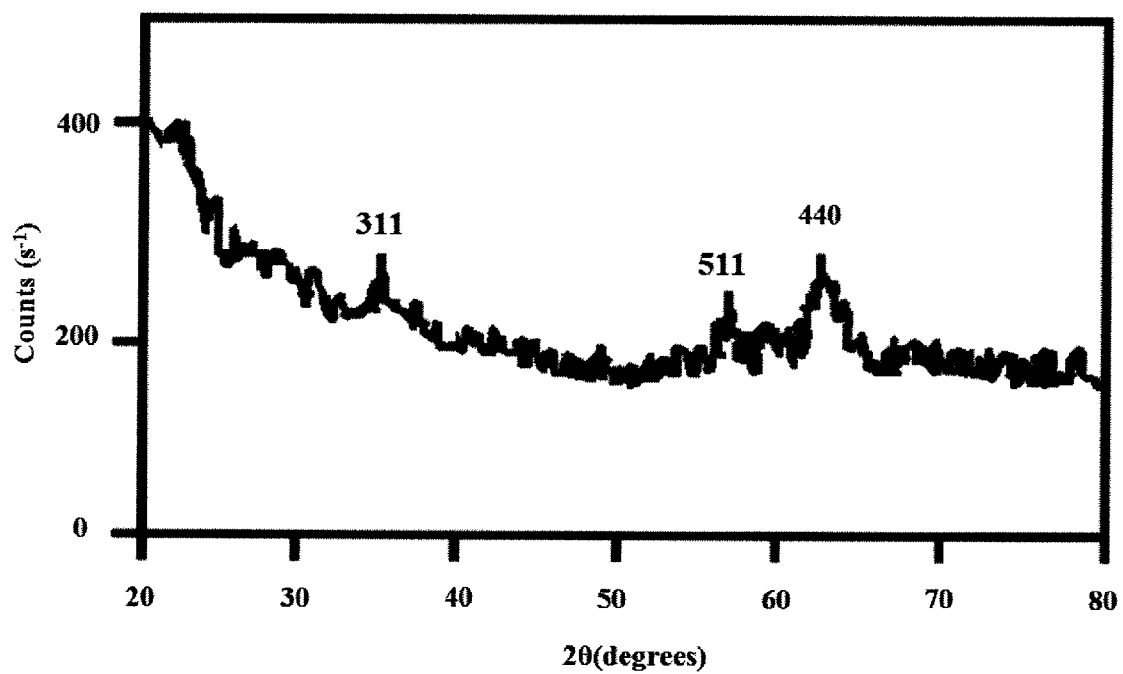
FIG. 5 depicts XRD pattern of nanocomposite

TEM results of nanocomposite and CHL-loaded nanocomposite showed agglomeration. SEM result of nanocomposite of DEAE-Cellulose/Fe is shown in FIG. 4 whereas SEM image of pure DEAE-Cellulose was taken from literature. The microfibrils have a length of 120-160 μm and diameter of 15-20 μM. The agglomeration in FIG. 4 although unclear, but shows deposition of Fe on the microfibrils and resembles with microfibrils given in literature. XRD pattern of all the peaks present in FIG. 5 is due to Fe can be effortlessly indexed as pure inverse spinel cubic structure, which competes well enough with the reported data. CHL-loaded nanocomposite has shown better activity than commercially available CHL (0.5%). The antibacterial activity of CHL-loaded nanocomposite showed sustained release of drug as reported by Prombutara P. and thus prolonging its action at the targeted site. All variants and their anti-bacterial activities are given in Table 1.

The zone of inhibitions of N+D 40 and N+D 60% were maximized, suggesting that maximum chloramphenicol was loaded when ethyl acetate was 40 and 60% in water respectively.

Commercially available CHL eye drops showed that almost the whole drug is released in 3-4 hours, which entails that frequent dosing after 4-5 hours is required for this preparation. Whereas CHL-loaded nanocomposite exhibited a biphasic release of the drug. The initial release was from 52 to 71% in the first 3 hours attributed by diffusion of the drug from polymer matrix; however CHL is released by the degradation of the polymer and diffusion of the drug in the later phase displaying a sustained release of the drug over 48 hours. The initial burst effect is due to the large surface area-to-volume ratio of the nanoparticles showed by Kumar G, Sharma S. et al. in their paper.

Figure 8:
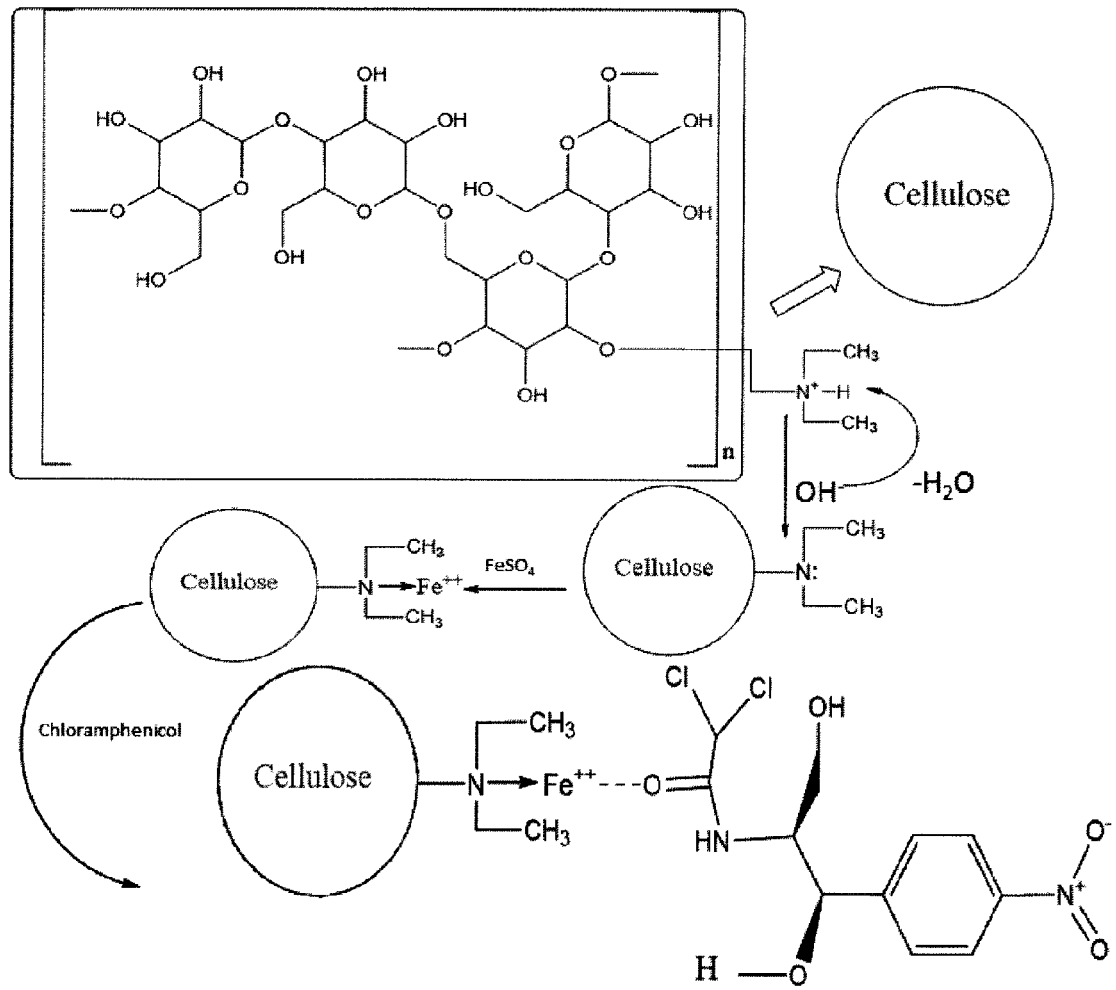
FIG. 8 depicts schematic diagram showing the interaction of nanocomposite and CHL.

FIG. 8 shows the proposed mechanism through which CHL interacted with the nanocomposite. The —OH group of the base NaOH attacked the electron deficient center i.e. N$^+$—H of the polymer and causes the removal of H$^+$ which leaves behind a lone pair of electron on the N of the polymer. The lone pair of electrons on N attracts Fe forming a coordinate covalent bond confirmed by the FTIR peak of Fe—N stretching vibration. The oxygen of carbonyl group present in CHL is attracted to the Fe which forms a temporary linkage between the two atoms. This linkage is cleaved during the degradation of polymer causing a sustained release of drug from the nanocomposite.

From the results obtained above, it could be stated the DEAE-Cellulose/Fe nanocomposite can be used to formulate sustained release preparations for targeted drug delivery of antibiotics. This polymer is biodegradable and biocompatible which increases interest in its use for better healthcare. Although further studies regarding pharmacokinetics, pharmacodynamics and clinical studies would provide a better understanding of the nanocomposite.

What is claimed is:

1. A method of preparing drug loaded polymeric iron nanoparticles comprising:
   a) mixing and sonicating an equimolar solutions of diethylaminoethyl cellulose and sodium hydroxide;
   b) adding to solution (a), a clear equimolar solution of ferrous sulfate and sulfuric acid to form nanocomposite precipitates;
   c) centrifuging the nanocomposite precipitates and drying it;
   d) dispersing the dried nanocomposite precipitates in water and adding a solution of a drug to be loaded, wherein the drug is chloramphenicol; and,
   e) centrifuging the mixture in step (d) and drying at above room temperature.

2. The method of claim 1, wherein diethylaminoethyl cellulose, sodium hydroxide, ferrous sulfate and sulfuric acid are used at a concentration of 0.01 M.

3. The method of claim 1, wherein the mixture of diethylaminoethyl cellulose and sodium hydroxide is sonicated for 30 minutes prior to use.

4. The method of claim 1, wherein the clear solution of ferrous sulfate and sulfuric acid is added at a rate of 0.1 mL/minutes.

5. The method of claim 1, wherein the precipitates in step (c) are centrifuged at 13,500 rpm and dried at 70 C.

6. The method of claim 1, wherein the mixture in step (e) is centrifuged at 13,500 rpm and dried at 40 C.

7. The method of claim 1, wherein the concentration of drug in the solution step (d) is 10 mg/8 mL.

\* \* \* \* \*